United States Patent
Kishimoto et al.

(10) Patent No.: US 9,144,670 B2
(45) Date of Patent: Sep. 29, 2015

(54) EXTERNAL PREPARATION KIT

(75) Inventors: Satoko Kishimoto, Yokohama (JP);
Chisato Takashimizu, Yokohama (JP);
Kazuhiro Yagyu, Kanonji (JP); Daisuke Yasugi, Kanonji (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 205 days.

(21) Appl. No.: 14/005,292

(22) PCT Filed: Mar. 27, 2012

(86) PCT No.: PCT/JP2012/057936
§ 371 (c)(1),
(2), (4) Date: Sep. 16, 2013

(87) PCT Pub. No.: WO2012/133409
PCT Pub. Date: Oct. 4, 2012

(65) Prior Publication Data
US 2014/0005615 A1    Jan. 2, 2014

(30) Foreign Application Priority Data
Mar. 28, 2011 (JP) ................................. 2011-070528

(51) Int. Cl.
*A61Q 19/00* (2006.01)
*A61M 35/00* (2006.01)
(Continued)

(52) U.S. Cl.
CPC .............. *A61M 35/00* (2013.01); *A61K 8/0204* (2013.01); *A61K 8/0208* (2013.01); *A61K 8/042* (2013.01);
(Continued)

(58) Field of Classification Search
CPC ..... A61K 47/36; A61K 47/38; A61K 8/0204; A61K 8/0208; A61K 8/042; A61K 8/60; A61K 8/65; A61K 8/73; A61K 8/731; A61K 8/732; A61K 8/737; A61K 8/8129; A61K 9/7076; A61M 35/00; A61Q 19/00
See application file for complete search history.

(56) References Cited

U.S. PATENT DOCUMENTS

| 2008/0014231 A1 | 1/2008 | Okano |
| 2010/0221306 A1 | 9/2010 | Tsujihata |
| 2010/0239621 A1 | 9/2010 | Tsujihata |

FOREIGN PATENT DOCUMENTS

| EP | 2210583 A1 | 7/2010 |
| JP | 63-297320 | 12/1988 |

(Continued)

OTHER PUBLICATIONS

Patent Abstracts of Japan, JP 2005-320264, 16 pages.
(Continued)

*Primary Examiner* — Ernst V Arnold
(74) *Attorney, Agent, or Firm* — Rankin, Hill & Clark LLP

(57) ABSTRACT

An external preparation kit is provided, which has a gel sheet having excellent water-releasing property and elongation, and a water-soluble sheet having excellent solubility. Thus, an external preparation kit according to the invention comprises:
(I) a gel sheet containing:
(a) 1-6% by mass of a composition comprising 10-80% by mass of carrageenan, 5-50% by mass of locust bean gum, 5-50% by mass of xanthan gum, and 5-50% by mass of mannan; and
(b) water; and
(II) a water-soluble sheet containing one or more component(s) selected from the group consisting of a cellulose derivative, polyvinyl alcohol, collagen, starch, gelatin, agar, and sugar.

20 Claims, 1 Drawing Sheet

(51) Int. Cl.

| | | |
|---|---|---|
| *A61K 47/36* | (2006.01) | |
| *A61K 8/60* | (2006.01) | |
| *A61K 8/73* | (2006.01) | |
| *A61K 8/65* | (2006.01) | |
| *A61K 8/81* | (2006.01) | |
| *A61K 47/38* | (2006.01) | |
| *A61K 8/02* | (2006.01) | |
| *A61K 8/04* | (2006.01) | |
| *A61K 9/70* | (2006.01) | |

(52) U.S. Cl.
CPC ... *A61K 8/60* (2013.01); *A61K 8/65* (2013.01); *A61K 8/73* (2013.01); *A61K 8/731* (2013.01); *A61K 8/732* (2013.01); *A61K 8/737* (2013.01); *A61K 8/8129* (2013.01); *A61K 9/7076* (2013.01); *A61K 47/36* (2013.01); *A61K 47/38* (2013.01); *A61Q 19/00* (2013.01)

(56) References Cited

FOREIGN PATENT DOCUMENTS

| JP | 08-290051 | 11/1996 |
|---|---|---|
| JP | 2002-087993 | 3/2002 |
| JP | 2003-113036 | 4/2003 |
| JP | 2003-277253 | 10/2003 |
| JP | 2005-225837 | 8/2005 |
| JP | 2005-320264 | 11/2005 |
| JP | 2006-056804 | 3/2006 |
| JP | 2007-153879 | 6/2007 |
| JP | 2008-092914 | 4/2008 |
| JP | 2009-067765 | 4/2009 |
| JP | 2009-073764 | 4/2009 |
| JP | 2009-541301 | 11/2009 |
| JP | 2010154898 A2 | 7/2010 |
| WO | WO 01/01950 * 1/2001 | ............... A61K 7/48 |

OTHER PUBLICATIONS

Patent Abstracts of Japan, JP 2007-153879, 9 pages.
Patent Abstracts of Japan, JP 2008-092914, 30 pages.
Patent Abstracts of Japan, JP 2003-277253, 6 pages.
Patent Abstracts of Japan, JP 2005-225837, 16 pages.
Patent Abstracts of Japan, JP 2003-113036, 9 pages.
Patent Abstracts of Japan, JP 08-290051, 7 pages.
Patent Abstracts of Japan, JP 2002-087993, 13 pages.
Patent Abstracts of Japan, JP 2009-067765, 10 pages.
Patent Abstracts of Japan, JP 2006-056804, 7 pages.
Patent Abstracts of Japan, JP 63-297320, 1 page, May 12, 1988.
PCT Notification of Transmittal of Translation of the International Preliminary Report on Patentability, International Application No. PCT/JP2012/057936 and Translation of the Written Opinion of the International Searching Authority, 6 pages.
Extended European Search Report dated Jan. 5, 2015 issued in the corresponding European patent application No. 12763468.1.

* cited by examiner (A)

(B)

EXTERNAL PREPARATION KIT

RELATED APPLICATIONS

This application claims the priority of Japanese Patent Application No. 2011-070528 filed on March 28, 2011, which are incorporated herein by reference.

FIELD OF THE INVENTION

The present invention relates to an external preparation kit composed of a gel sheet and a water-soluble sheet, particularly improvement in the water-releasing property and the strength of the gel sheet, and the solubility of the water-soluble sheet.

BACKGROUND OF THE INVENTION

Conventionally, to provide a beauty effect such as moisturizing of the skin or to cool or reduce inflammation of an affected area, a sheet-like external preparation that is to be attached to the skin in use has been used.

As such an external preparation, particularly in the field of cosmetics, sheet packs in which nonwoven fabric or the like is impregnated with an aqueous solution of an active ingredient are generally used, but this type of preparation has problems in the retention of water containing an active ingredient and sense of use.

In recent years, the following two types have therefore attracted attention as a more effective sheet-like external preparation.

The first type is an external preparation in which an active ingredient is retained in a gel sheet using a polysaccharide such as agar, carrageenan, locust bean gum, and mannan.

As a sheet-like external preparation of this type, for example, Patent Literature 1 (Japanese Unexamined Patent Application Publication No. H08-290051) discloses a hydrogel base obtainable by blending glucomannan and locust bean gum or carrageenan. The hydrogel base is very unlikely to lose shape and stable in a weakly acidic region including the human skin.

In addition, Patent Literature 2 (Japanese Unexamined Patent Application Publication No. 2002-87993) discloses an external gel composition containing carrageenan and/or mannan, and a polysaccharide thickener (for example, gellan gum, agar, and agarose) that can alone form a gel with a melting point of 80° C. or higher. The external gel composition has an excellent sense of use and appearance and high storage stability.

Moreover, Patent Literature 3 (Japanese Unexamined Patent Application Publication No. 2009-67765) discloses that a water-soluble gel for mask having a total blending amount of carrageenan and locust bean gum of 2.0% by weight or less is excellent in form retention and flexibility and is easily attached by adhering to provide adhesion.

Also, the second type is an external preparation having a dry film-like sheet containing a water-soluble substance such as a cellulose derivative, starch, and sugar as an active ingredient. For this type of external preparation, after the sheet is attached to the skin, water is added to dissolve the film and thereby an active ingredient is supplied to the skin.

The above gel sheet has such advantages that the gel is retained in a sheet-like form and thus stable and easy to handle, and the gel sheet tightly adheres to the skin due to retention of water in the gel. On the other hand, the high form retention of the gel sheet has made it difficult to dissolve the active ingredient in the gel into the skin as intended.

In addition, in the case of a dry film-like sheet, when the film is dissolved, all the active ingredients in the film can be supplied to the skin. However, the adhesion of the film to the skin is poor, and the film is dissolved easily when water is supplied. This type of film has had difficulties in handling and application to the skin as intended.

For this problem, an external preparation kit with which two or more different sheets are laminated and applied to the skin has been proposed.

For example, Patent Literature 4 (Japanese Unexamined Patent Application Publication (Translation of PCT Application) No. 2009-541301) discloses a treatment article with which, by covering the entire face with a water-insoluble base such as nonwoven fabric after the above described dry film (water-soluble film) type sheet is attached to a part of the face that needs intensive care, the film is dissolved by the water contained in the nonwoven fabric.

In addition, Patent Literature 5 (Japanese Unexamined Patent Application Publication No. 2006-56804) discloses a mask sheet which has a dried water-soluble film containing a beauty component and a gel sheet laminated on the film and with which the liquid in the gel sheet moves to dissolve the water-soluble sheet and the beauty component is dissolved.

Moreover, Patent Literature 6 (Japanese Unexamined Patent Application Publication No. S63-297320) describes a composite patch with which a hydrogel composed of a water-soluble polymer such as polyacrylic acid, polyvinyl alcohol, and polyvinylpyrrolidone and water is placed on a sheet-formed water-soluble drug-containing hydrophilic base for achieving attachment by adhering and layering on the skin.

DISCLOSURE OF THE INVENTION

Problem To Be Solved By The Invention

However, in the technique in Patent Literature 4, in which a water-insoluble base such as nonwoven fabric is placed on a water-soluble film, the degree of dissolution of the water-soluble sheet is not seen from outside, and conventional nonwoven fabric that is easily dried has made it difficult to adjust a water content of the water-soluble film In addition, in the case of a gel sheet that is placed on a soluble film in Patent Literatures 5 and 6, since the shape and the size of the water-soluble film are the same as those of the gel sheet, there has been a problem in adhesion of the film to the skin and the solubility of the film by the gel sheet. Also, in terms of supplying sufficient water to dissolve the film, there is room for improvement in the water-releasing property of the gel sheet. Moreover, the gel sheet is required to have appropriate elongation to be applied to the sites having various shapes, and to respond to exercise of the site that the gel sheet is being applied. However, a gel sheet having excellent water-releasing property and elongation still has not been obtained.

The present invention is made in light of the above problems and aims to provide an external preparation kit having a gel sheet having excellent water-releasing property and elongation, and a water-soluble sheet having excellent solubility.

Means To Solve The Problem

To solve the above problems, the inventors of the present invention have investigated eagerly and found that a gel sheet formed by a composition composed of a specific gelling component shows excellent water-releasing property and elongation, and by covering a water-soluble sheet with the gel sheet, the solubility of the water-soluble sheet is improved substantially and the component contained in the water-soluble sheet is supplied to the skin efficiently, leading to the completion of the present invention.

Thus, an external preparation kit according to the present invention comprises:

(I) a gel sheet containing:
(a) 1-6% by mass of a composition comprising 10-80% by mass of carrageenan, 5-50% by mass of locust bean gum, 5-50% by mass of xanthan gum, and 5-50% by mass of mannan; and
(b) water; and
(II) a water-soluble sheet containing one or more component(s) selected from the group consisting of a cellulose derivative, polyvinyl alcohol, collagen, starch, gelatin, agar, and sugar.

Also, it is preferred that, in the external preparation kit, the composition (a) contains carrageenan at 25-35% by mass, locust bean gum at 20-30% by mass, xanthan gum at 20-30% by mass, and mannan at 15-25% by mass.

Also, it is preferred that, in the external preparation kit, a blending amount of the composition (a) is 1-2.5% by mass.

Also, it is preferred that, in the external preparation kit, a weight ratio between locust bean gum and xanthan gum is from 2:1 to 1:2.

Also, it is preferred that, in the external preparation kit, the (II) water-soluble sheet contains hydroxypropyl methylcellulose.

Also, it is preferred that, in the external preparation kit, an area of a surface on a side contacting the (II) water-soluble sheet of the gel sheet (I) is larger than an area of a surface on a side contacting the gel sheet (I) of the water-soluble sheet.

Also, a method of using the external preparation kit according to the present invention comprises laying a gel sheet (I) on a water-soluble sheet (II) so that the gel sheet (I) covers a whole surface on one side of the water-soluble sheet (II) completely.

Effect Of The Invention

According to the present invention, a gel sheet having excellent water-releasing property and elongation dissolves a water-soluble sheet and supplies a component contained in the water-soluble sheet effectively to the skin. In addition, the dissolved water-soluble sheet is retained between the gel sheet and the skin in a tightly adhered state and high efficacy as a mask is thus expected.

DESCRIPTION OF REFERENCE NUMBERS

Figure 1:
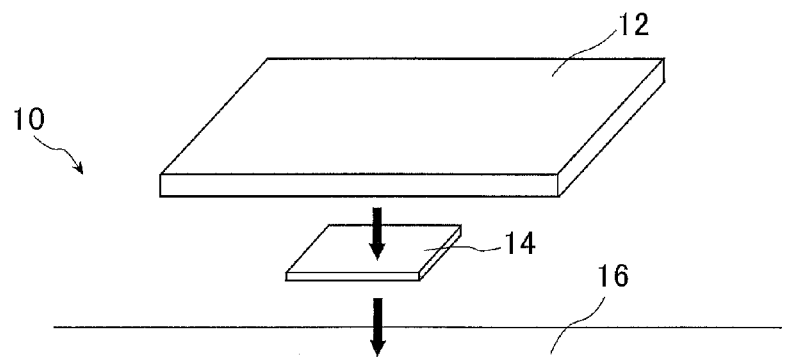
FIG. 1 illustrates an embodiment of the present invention.

10 External preparation kit
12 Gel sheet
14 Water-soluble sheet
16 Skin

BEST MODE FOR CARRYING OUT THE INVENTION

The external preparation kit according to the present invention has a gel sheet (I) and a water-soluble sheet (II), and is used by placing the gel sheet on the water-soluble sheet.

First, the components constituting each sheet are explained.

(I) Gel Sheet

The gel sheet of the present invention is a gel sheet in which water is retained in the gel structure, and is composed of (a) a composition containing carrageenan, locust bean gum, xanthan gum, and mannan, and (b) water.

The composition as the component (a) contains four polysaccharide thickeners, that is, carrageenan, locust bean gum, xanthan gum, and mannan, at 10-80% by mass, 5-50% by mass, 5-50% by mass, and 5-50% by mass, respectively, preferably at 25-35% by mass, 20-30% by mass, 20-30% by mass, and 15-25% by mass, respectively, with respect to the composition. The composition acts as a gelling agent for (b) water (an aqueous solution of a water-soluble component).

In addition, the gel sheet (I) contains the composition as the component (a) at 1-6% by mass, preferably 1-2.5% by mass. Therefore, when the composition as the component (a) is blended at a content in the range of 1-6% by mass in the gel sheet, the content of carrageenan in the gel sheet is 0.1-4.8% by mass, preferably 0.25-2.1% by mass. Similarly, the blending amount of locust bean gum in the gel sheet is 0.05-3% by mass, preferably 0.2-1.8% by mass. The content of xanthan gum in the gel sheet is 0.05-3% by mass, preferably 0.2-1.8% by mass. The blending amount of mannan in the gel sheet is 0.05-3% by mass, preferably 0.15-1.5% by mass Also, when the composition as component (a) is blended in the gel sheet at a content in the range of 1-2.5% by mass, the content of carrageenan in the gel sheet is 0.1-2% by mass, preferably 0.25-1.5% by mass. Similarly, the blending amount of locust bean gum in the gel sheet is 0.05-1.25% by mass, preferably 0.2-1.0% by mass. The content of xanthan gum in the gel sheet is 0.05-1.25% by mass, preferably 0.2-1.0% by mass. The blending amount of mannan in the gel sheet is 0.05-1.25% by mass, preferably 0.15-1.0% by mass.

In the present invention, a gel sheet having an extremely high water-releasing property and appropriate elongation can be obtained by using the above four polysaccharide thickeners at contents within the above described range. Although blending of all the four polysaccharide thickeners is considered to be related to achieving high water-releasing property and elongation, the water-releasing property of the gel sheet tends to decline largely particularly when the content of carrageenan exceeds 4.8% by mass with respect to the gel sheet.

Also, particularly when the content of mannan is less than 0.05% by mass with respect to the gel sheet, the form retention of the gel sheet becomes difficult, and when the content of mannan exceeds 3% by mass, the gel sheet tends to become too hard to be attached to the skin.

In addition, the elongation of the gel sheet of the present invention can be changed by a mass ratio of xanthan gum to locust bean gum in the composition as component (a). The elongation of the gel sheet becomes highest when the mass ratio is 1:1 (locust bean gum:xanthan gum). In contrast, as the mass ratio moves away from 1:1, the elongation becomes lower, but as long as the contents of the two components are within the above described range, the elongation is maintained at 200% or more, which is sufficient to use. Therefore, within the above described content range, by adjusting the mass ratio of locust bean gum and xanthan gum, a gel sheet having high water-releasing property as intended can be obtained. In the present invention, in particular, locust bean gum and xanthan gum are suitably used at the ratio of 2:1 to 1:2 to obtain a gel sheet having excellent elongation.

The external preparation kit of the present invention has such a form that a water-soluble sheet is dissolved by water that is retained in a gel sheet thickened and gelled by the above polysaccharide thickeners and dissolved from the gel sheet when used. In addition, by utilizing the adhesion of the gel sheet retaining water to the skin, the water-soluble sheet can be retained and tightly adhered between the skin and the gel sheet. Therefore, a sufficient amount of (b) water is preferably blended in the gel sheet to tightly adhere the gel sheet to the skin and to dissolve the water-soluble sheet with water released from the gel sheet. The component (b) is a balance of the gel sheet excluding the component (a), and the content of the component (b) depends on the blending amount of the component (a). Considering that the water contained in the gel sheet dissolves the water-soluble sheet, the gel sheet preferably contains about one to ten times the volume of the water-soluble sheet. In the present invention, as long as the blending amount of the component (a) is within the specific range described later, the content of the component (b) can be a quantity sufficient to dissolve the water-soluble sheet.

Here, the above described component (b) may also contain water-soluble components usually used in cosmetics, pharmaceutical preparations, and quasi drugs within the range that does not degrade the effect of the present invention.

Examples of the above described water-soluble components include lower alcohols, polyalcohols, and acids and salts.

Examples of lower alcohols include ethanol, propanol, isopropanol, isobutyl alcohol, t-butyl alcohol.

Examples of polyalcohols include dihydric alcohols (e.g. ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol); trihydric alcohols (e.g. glycerin, trimethylolpropane and 1,2,4-hexanetriol); polyhydric alcohol polymers (e.g diethylene glycol, dipropylene glycol, triethylene glycol, polypropylene glycol, tetraethylene glycol, diglycerin, polyethylene glycol, triglycerin, tetraglycerin and polyglycerin); polyhydric alcohol alkyl ethers (e.g. ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); polyhydric alcohol alkyl esters (e.g. ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (e.g. chimyl alcohol, selachyl alcohol, and butyl alcohol); sugar alcohols (e.g. xylitol, pentaerythritol, sorbitol, maltitol, maltotriose, mannitol, sucrose, erythritol, glucose, fructose, starch sugar, maltose, xylitol, and starch sugar reduced alcohol); glysolid; tetrahydrofurfuryl alcohol; POE tetrahydrofurfuryl alcohol; POP butyl ether; POP/POE butyl ether; tripolyoxypropylene glycerin ether; POP glycerin ether; POP glycerin ether phosphate; POP/POE pentaerythritol ether; and polyglycerin.

Examples of acids and salts include organic acids and organic salts (amino acid, amino-acid salt and oxyacid salt), and inorganic salts (sodium chloride, potassium chloride, magnesium chloride, and sodium hydrogencarbonate).

In the present invention, particularly, in terms of providing a moisturizing property to the gel sheet and giving a moist feeling to the skin after use, and compatibility to the (II) water-soluble sheet described later, the blending of a polyalcohol(s) is preferred, more preferably dihydric alcohol and/or glycerin, even more preferably glycerin. The blending amount, for example, in the case of a dihydric alcohol (for example, 1,3-butylene glycol, dipropylene glycol), is preferably approximately 1-15% by mass each with respect to the gel sheet, and in the case of glycerin, is preferably approximately 1-10% by mass with respect to the gel sheet.

In addition, in the component (b), in addition to the above water-soluble component(s), oil-soluble component(s) such as perfume may be blended in by emulsification and solubilization using a surfactant.

Additionally, each of the above components may be added alone or in combination of two or more.

In the present invention, the above described gel sheet is produced by forming a gel composition into a sheet-like form. The gel composition is obtained by adding/mixing (a) a composition containing carrageenan, locust bean gum, xanthan gum, and mannan to an aqueous solution of the above water-soluble component and the like dissolved in (b) water as necessary, to give a concentration of 1-6% by mass, preferably 1-2.5% by mass. Additionally, in the above described production, the composition may be heated/cooled as necessary.

For the formation of a sheet-like form, a variety of methods can be used, such as rolling and cooling of the obtained gel composition, filling the gel composition before cooling into a container having the intended shape and then cooling, or solidifying to a block-like form and then cutting into a sheet-like form.

The thickness of the formed gel sheet is not specifically limited, but the thickness is preferably adjusted to be sufficient to allow the gel sheet to be kept in a tightly adhered state and to supply water necessary to dissolve the water-soluble sheet. In general, the thickness of 0.1-3.0 mm is sufficient to have an effect as the gel sheet of the present invention.

Also, the size of the gel sheet is preferably large enough to cover the water-soluble sheet (II) described later completely, that is, the area of a surface on a side contacting the water-soluble sheet of the gel sheet is preferably formed larger than the area of a surface on a side contacting the gel sheet of the water-soluble sheet. Moreover, the gel sheet is preferably translucent to transparent such that the degree of dissolution of the water-soluble sheet over time can be observed when the water-soluble sheet is covered by the gel sheet. Additionally, there are no limitations on the shape of the gel sheet, and the shape of the external preparation of the present invention may be selected depending on the site to be applied or the intended use.

(II) Water-Soluble Sheet

The water-soluble sheet of the present invention is a film-like sheet which is dissolved in water at ordinary temperature and contains a film-forming component selected from a cellulose derivative, polyvinyl alcohol, collagen, starch, gelatin, agar, and sugar.

Examples of cellulose derivatives include water-soluble cellulose ethers such as hydroxyalkyl celluloses (e.g. methylcellulose, hydroxyethyl cellulose, hydroxypropyl cellulose, hydroxypropyl methylcellulose, hydroxypropyl hydroxyethylcellulose, hydroxyethyl methyl cellulose, ethylcellulose, and carboxymethylcellulose).

Examples of starches include native starch; etherified starches (e.g. hydroxyalkylated starches such as hydroxypropylated starch, hydroxyethylated starch, hydroxymethylated starch, and hydroxypropylmethylated starch); esterified starches (e.g. acetylated starch); organic esterified starches; and modified starches thereof such as cross-linked product, oxidative product, enzyme-transformed product and acid hydrolysate.

Examples of sugars include water-soluble polysaccharides such as pullulan, elsinan, sodium alginate, pectin, tamarind gum, xanthane gum, guar gum, tara gum, locust bean gum, arabinogalactan, gum arabic, chitosan, amylase, amylopectin, dextran, mannan, and glycosyl trehalose.

The above film-forming component may be added alone or in combination of two or more. In the present invention, the use of water-soluble cellulose ether, particularly hydroxypropyl methylcellulose is preferred.

The blending amount of the above film-forming component(s) in the water-soluble sheet may be appropriately determined depending on the film-forming component used, and is preferably 40-70% by mass to the water-soluble sheet, more preferably 50-70% by mass.

The water-soluble sheet of the present invention can be produced by applying/drying an aqueous solution containing the above components on the base and forming the base to a flat sheet-like form. The thickness of the water-soluble sheet after drying is preferably 10-60 µm, more preferably 20-40 µm. When the thickness of the water-soluble sheet exceeds 60 µm, the sheet may not be dissolved sufficiently when used. When the thickness of the sheet is less than 10 µm, the effect of the blended components on the skin may not be sufficient.

The water-soluble sheet is preferably formed in such a size that the sheet can be covered completely by the above gel sheet (I), that is, the area of a surface on a side contacting the gel sheet of the water-soluble sheet is smaller than the area of a surface on a side contacting the water-soluble sheet of the gel sheet. If the water-soluble sheet is not covered completely by the gel sheet, the water exuding from the gel sheet is not sufficiently supplied to the water-soluble sheet and the dissolution of the water-soluble sheet and the effect of the components contained may be imperfect. In addition, since the water-soluble sheet is not retained by the gel sheet, the adhesion of the sheet to the skin may be insufficient.

In addition to the above essential components, components generally used in cosmetics, medicines and non-medicinal products can be blended in the water-soluble sheet according to the present invention so long as the effectiveness of the present invention is not undermined.

Examples of such components include humectants such as 1,3-butylene glycol, polyethylene glycol, propylene glycol, dipropylene glycol, hexylene glycol, glycerin, diglycerin, xylitol, maltitol, maltose, D-mannitol, glycosyl trehalose and hyaluronan; lower alcohols such as ethanol and propanol; ultraviolet absorbers such as benzoic acid-based ultraviolet absorbers (e.g. para-aminobenzoic acid), anthranilic acid-based ultraviolet absorber (e.g. methyl anthranilate), salicylic acid-based ultraviolet absorber (e.g. octyl salicylate and phenyl salicylate), cinnamic acid-based ultraviolet absorbers (e.g. isopropyl-p-methoxy cinnamate, octyl-p-methoxy cinnamate, and di-p-methoxycinnamic acid-mono-2-ethylhexanoic acid glyceryl), benzophenone-based ultraviolet absorbers (e.g. 2,4-dihydroxybenzophenone, 2-hydroxy-4-methoxybenzophenone, and 2-hydroxy-4-methoxybenzophenone-5-sulfonic acid), urocanic acid, 2-(2'-hydroxy-5'-methylphenyl) benzotriazol, 4-tert-butyl-4'-methoxybenzoylmethane; sequestrants such as edetate sodium, sodium metaphosphate and phosphoric acid; sequestrants such as ascorbic acid, alpha-tocopherol, dibutylhydroxytoluene, and butylhydroxyanisol; pH adjusters such as potassium hydroxide, citrate and acetate; chelators; preservatives such as paraben, phenoxyethanol, and chlorhexidine gluconate; fragrances; pigments; amino acids and amino-acid salts; inorganic salts such as sodium salt, calcium salt and potassium salt; powders such as talc, silica gel, zinc oxide, and titanium oxide.

Also, oils such as hydrocarbon oils (e.g. vaseline, squalane and microcrystalline wax), ester oils (e.g. jojoba oil, spermaceti, and carnauba wax), triglycerides (e.g. olive oil and beef tallow), higher alcohols (e.g. cetanol, oleyl alcohol, and stearyl alcohol), higher fatty acids (e.g. stearic acid and oleic acid), silicone oils (e.g. dimethylpolysiloxane, decamethylcyclopentasiloxane, and polyether-modified silicone) and other oil-soluble components may be added by being emulsified or solubilized with surfactants.

Examples of surfactants include nonionic surfactants such as fatty acid monoglyceride and polyoxyethylene hydrogenated castor oil; anionic surfactants such as sodium lauryl sulfate and alkyl sulfosuccinate; cationic surfactants such as quaternary alkylamine salts; ampholytic surfactants such as alkyl betaine; polymeric surfactants such as alkyl modified carboxyvinyl polymer.

Furthermore, various drugs can be blended according to the purpose in the film-shaped external preparation composition to provide drug efficacy.

Examples of the drug include vitamins such as vitamin A oil, retinol, retinol palmitate, inositol, pyridoxine hydrochloride, benzyl nicotinate, nicotinic acid amide, dl-α-tocopherol nicotinate, ascorbic acid magnesium phosphate, ascorbic acid-2-glucoside, vitamin D2 (ergocalciferol), potassium2-L-ascorbic acid diphosphate, dl-α-tocopherol, dl-α-tocopherol acetate, pantothenic acid, biotin, pyridoxine hydrochloride, CoQ10; an anti-inflammatory drug such as tranexamic acid, allantoin, glycyrrhizic acid salt, azulene, lysozyme chloride; a whitening agent such as arbutin and kojic acid; an astringent such as zinc oxide and tannin; sulphur; an α-lipoic acid; menthol: a tonic such as a γ-oryzanol, Korean ginseng and a sterol glycoside; an osmoregulating chemical; an antihistamine; a steroid hormone; a disinfectant; an antifungal agent; a vasoprotective drug; an antioxidant; a hypopigmentation drug; a desensitizer; an immunomodulator; an anti-aging drug; an anti-wrinkle agent; a sebum absorption agent; an antibiotic; a deodorant; and a fabric softener.

In addition, the above drugs can be used not only in a free form but also in form of a salt with an acid or a base when the drugs can form a salt in an ester form when the drugs have a carboxylic acid functional group.

In the present invention, in view of providing a moist feeling after use, the blending of a moisturizing agent(s), particularly, one or more of 1,3-butylene glycol, dipropylene glycol, and glycerin is preferred. The blending amount of the total of the above moisturizing agents is preferably 0.1-30% by mass.

In the external preparation kit according to the present invention, the gel sheet (I) may be placed on the water-soluble sheet (II) so that the gel sheet (I) covers a surface of on side of the water-soluble sheet (II) completely, when used.

FIG. 1 illustrates an embodiment of the external preparation kit of the present invention. An external preparation kit 10 is composed of a gel sheet 12 and a water-soluble sheet 14 and constituted such that the gel sheet 12 can cover the water-soluble sheet 14 completely when the water-soluble sheet 14 is placed on the skin 16.

Additionally, the gel sheet 12 of the present invention is generally transparent so that the state of dissolution of the water-soluble sheet 14 under the gel sheet 12 can be seen while the external preparation kit 10 remains to be used. In addition, since the water-soluble sheet 14 is smaller than the gel sheet 12, even when the dry water-soluble sheet 14 before use is unlikely to adhere to the skin 16, the water-soluble sheet 14 can be retained on the surface of the skin 16 in a tightly adhered state by placing the gel sheet 12 thereon.

Additionally, in this case, a surface of the side contacting the water-soluble sheet 14 of the gel sheet 12 may be in contact with the skin 16.

Figure 2:
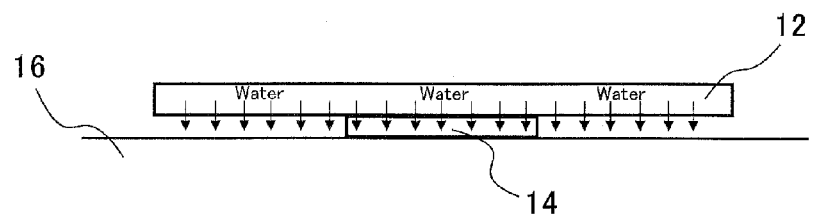
FIG. 2 is a sectional view of the external preparation of the present invention applied to the skin.
Figure 2:
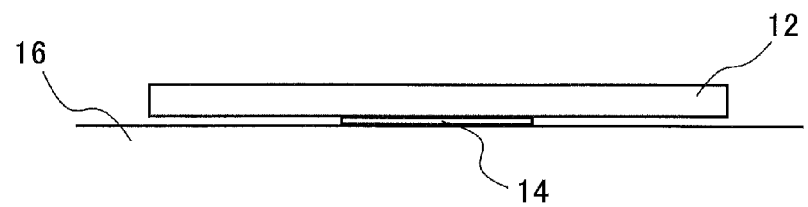

FIG. 2 illustrates a sectional view of the above described external preparation kit applied to the skin (A) shows the state immediately after use, and (B) shows the state of the water-soluble sheet after dissolution.

As illustrated in FIG. 2 (A), water released from the gel sheet 12 covering the water-soluble sheet is supplied to the water-soluble sheet 14. The dry water-soluble sheet before use is gradually dissolved in the water and turns into a liquid (or gel) at the end. The components in the water-soluble sheet, as shown in FIG. 2 (B), remains retained between the gel sheet 12 and the skin 16 even in a liquid state and is hardly dried. Efficient and effective face pack by the components in the water-soluble sheet can therefore be provided to the skin under the gel sheet.

The use of the external preparation kit according to the present invention is not particularly limited as far as the effect of the present invention is not degraded, but the external preparation kit is suitably used for cosmetic and medical uses.

The product forms for cosmetic and medical uses of the present invention depending on the component blended in the gel sheet and the water-soluble sheet include a moisturizing sheet, a rough skin improvement sheet, a wrinkle smoothing sheet, a corneum removing sheet, a pore care sheet, a body moisturizing sheet, a body whitening agent, a sunburn treatment agent, a wound/burn protection sheet, a antifebrile sheet, an anti-itch sheet, a suppuration prevention drug, and an acne-preventing/treatment agent.

In addition, besides the above forms that directly exert the action to the surface of the skin and its periphery, there are product forms with which drugs and the like are administered percutaneously to target a site away from the applied site.

The following Examples are illustrative of the present invention and are not limitations thereof Unless otherwise noted, the blending amount is expressed in % by mass with respect to the composition in which a component is added.

EXAMPLES

Gel composition shown in the following Test Examples 1-1 to 1-3 were formed into a circular gel sheet with a diameter of 70 mm (thickness 1.0 mm). In addition, a dry water-soluble sheet prepared according to the following method of production was formed into a round sheet with a diameter of 30 mm (thickness 30 μm). The water-soluble sheet was placed on a transparent plate and the gel sheet was placed thereon. The state of dissolution of the water-soluble sheet after 5, 10, 15, 20, 25, and 30 minutes was evaluated according to the following criteria. The results are shown in Table 1.

Test Example 1-1

| (Component) | (mass %) |
|---|---|
| Sodium polyacrylate | 5.0 |
| Carboxymethylcellulose sodium | 5.0 |
| Polyacrylic acid | 1.0 |
| Castor oil | 0.4 |
| Tartaric acid | 0.4 |
| Magnesium aluminometasilicate | 0.2 |
| Dipropylene glycol | 5.0 |
| 1,3-butylene glycol | 5.0 |
| Preservative | appropriate amount |
| Water | Balance |

Test Example 1-2

| (Component) | (mass %) |
|---|---|
| Agar | 4.0 |
| Xanthane gum | 0.5 |
| Locust bean gum | 0.5 |
| Dipropylene glycol | 5.0 |
| 1,3-butylene glycol | 5.0 |
| Preservative | appropriate amount |
| Water | Balance |

Test Example 1-3

| (Component) | (mass %) |
|---|---|
| Carrageenan | 1.0 |
| Mannan | 0.5 |
| Xanthane gum | 0.5 |
| Locust bean gum | 0.5 |
| Dipropylene glycol | 5.0 |
| 1,3-butylene glycol | 5.0 |
| Preservative | appropriate amount |
| Water | Balance |

Prescription of Water-Soluble Sheet

| (Component) | (mass %) |
|---|---|
| Hydroxypropyl methylcellulose | 60.0 |
| 1,3-butylene glycol | 15.0 |
| Dipropylene glycol | 5.0 |
| PEG-60 hydrogenated castor oil | 1.5 |
| Preservative | appropriate amount |
| Water | Balance |

(Method of Production)

The other components were added to water and then the mixture was mixed by stirring. The resulting aqueous solution was applied to a base and dried to obtain a dry film-like water-soluble sheet.

<Evaluation Criteria>

Solubility of Water-Soluble Sheet

The state of dissolution of the water-soluble sheet was observed visually through the gel sheet. The solubility was evaluated according to the following criteria.

○: The water-soluble sheet is completely dissolved with no shape remaining.
Δ: The water-soluble sheet is dissolved, but the shape is maintained.
X: The water-soluble sheet is not dissolved or hardly dissolved.

TABLE 1

Solubility of water-soluble sheet

| 5 minutes later | 10 minutes later | 15 minutes later | 20 minutes later | 25 minutes later | 30 minutes later |
|---|---|---|---|---|---|
| Test Example 1-1 | | | | | |
| x | x | x | x | x | x |
| Test Example 1-2 | | | | | |
| x | Δ | Δ | Δ | Δ | Δ |
| Test Example 1-3 | | | | | |
| Δ | ○ | ○ | ○ | ○ | ○ |

As shown in Table 1, the gel sheet in Test Example 1-3 in which carrageenan, locust bean gum, xanthan gum, and mannan were blended had high water-releasing property and the water-soluble sheet was dissolved rapidly.

On the other hand, in Test Example 1-1 in which polyacrylic acid or carboxy vinyl polymer was used as a gelling agent and in Test Example 1-2 in which agar, xanthan gum, and locust bean gum were used, the gel sheet hardly released water and the water-soluble sheet could not be dissolved completely within 30 minutes.

Moreover, for the gel sheet (thickness 0.8 mm) each having the composition shown in Table 2 in Test Examples 2-1 to 2-7, the following tests were conducted for each gel sheet to evaluate the water-releasing property (volume of bleeding), elongation (elongation of gel), and transparency. The results are shown in Table 2.

Evaluation Test of Water-Releasing Property (Volume of Bleeding)
(1) Five sheets of hardened filter paper with a diameter of 95 mm (diameter of retained particles 1 μm) were put into a petri dish with a diameter of 100 mm.
(2) The dish set (1) was put into a thermostat set at 32° C. and the temperature was kept at a constant temperature.
(3) The petri dish set was removed from the thermostat and the weight was measured (designated as weight (A)).
(4) After the measurement of the weight, the dish set was put into the thermostat again for 15 minutes to make the temperature homogenous.
(5) The petri dish was removed from the thermostat and a gel sheet formed into a circular form with a diameter of 65 mm was put into the petri dish and the weight was measured (designated as weight (B)), and then the dish was put into the thermostat.
(6) After 15 minutes, the petri dish set was removed from the thermostat and the gel sheet was removed from the petri dish and the weight was measured (designated as weight (C)).
(7) The volume of bleeding was calculated in accordance with {(weight (A)−weight (C))/weight (B)}×100(%).
(8) The number of test samples in each Test Example was 10. The mean value of volumes of bleeding calculated was evaluated according to the following criteria.
○: The mean volume of bleeding: 18% or higher
Δ: The mean volume of bleeding: 12% or higher and less than 18%
X: The mean volume of bleeding: less than 12%
Evaluation Test of Elongation (Elongation of Gel)
(1) A gel sheet was cut into 40 mm in width.
(2) A tensile test of the cut gel plate was conducted using an autograph device (Shimadzu Corporation AGS-N-100N) under the conditions of a chuck distance of 150 mm and a tensile speed of 300 mm/min to measure the elongation of the gel.
(3) The number of test samples in each Test Example was 10. The mean value of elongations measured was evaluated according to the following criteria.
○: The mean elongation: 200% or higher
Δ: The mean elongation: 150% or higher and less than 200%
X: The mean elongation: less than 150%
Transparency Test
The transparency of the gel sheet placed on the water-soluble sheet prepared by the above described method of production was confirmed visually according to the following criteria.
○: The gel sheet is transparent and the water-soluble sheet can be seen through the gel sheet
Δ: The gel sheet is a little opaque and the water-soluble sheet is difficult to be seen through the gel sheet
X: The gel sheet is opaque and the water-soluble sheet cannot be seen through the gel sheet

TABLE 2

| | Test Example | | | | | | |
|---|---|---|---|---|---|---|---|
| | 2-1 | 2-2 | 2-3 | 2-4 | 2-5 | 2-6 | 2-7 |
| Locust bean gum | 0.5 | 0.5 | — | — | — | — | — |
| Xanthane gum | 0.5 | 0.5 | 0.5 | 0.9 | 0.9 | 0.5 | 0.5 |
| Mannan | 0.3 | 0.4 | 0.3 | 0.3 | 0.5 | 0.5 | 1.0 |
| Carrageenan | 0.6 | 0.6 | 0.6 | 0.6 | 0.6 | 0.6 | 0.6 |
| Glycerin | 5.0 | 7.0 | 5.0 | 5.0 | 5.0 | 5.0 | 5.0 |
| 1,3-butylene glycol | 3.0 | 3.0 | 3.0 | 3.0 | 3.0 | 3.0 | 3.0 |
| Dipropylene glycol | 5.0 | 3.0 | 5.0 | 5.0 | 5.0 | 5.0 | 5.0 |
| PEG-60 hydrogenated castor oil | 0.3 | 0.3 | 0.3 | 0.3 | 0.3 | 0.3 | 0.3 |
| Preservative | Appropriate amount | Appropriate amount | Appropriate amount | Appropriate amount | Appropriate amount | Appropriate amount | Appropriate amount |
| Fragrance | Appropriate amount | Appropriate amount | Appropriate amount | Appropriate amount | Appropriate amount | Appropriate amount | Appropriate amount |
| Water | Balance | Balance | Balance | Balance | Balance | Balance | Balance |
| Water-releasing property | ○ | ○ | ○ | Δ | Δ | Δ | ○ |
| Elongation of gel | ○ | ○ | Δ | Δ | Δ | Δ | ○ |
| Transparency | ○ | ○ | ○ | ○ | Δ | Δ | Δ |

As shown in Test Examples 2-1 and 2-2, water-releasing property, elongation, and transparency were all improved by using the four components, that is, locust bean gum, xanthan gum, mannan, and carrageenan to prepare a gel sheet. However, as shown in Test Examples 2-3 to 2-7, a gel sheet excellent in all of water-releasing property, elongation, and transparency could not be obtained in the absence of locust bean gum, even when the blending amounts of the other three components were adjusted and polyalcohols were added.

Therefore, in the present invention, a gel sheet preferably contains carrageenan, locust bean gum, xanthan gum, and mannan.

The above water-releasing property (volume of bleeding) and elongation (elongation of gel) of the gel sheets (thickness 0.8 mm) in Test Examples 3-1 to 3-7 having the compositions shown in Table 3 were evaluated. The results are shown in Table 3.

of the above composition was less than 1% by mass, the elongation was especially poor, and in Test Example 3-7 in which the blending amount exceeded 6% by mass, the water-releasing property was especially poor.

Therefore, in the present invention, the gel sheet contains preferably 1 to 6% by mass, especially preferably 1-2.5% by mass of the composition containing 25-35% by mass of carrageenan, 20-30% by mass of locust bean gum, 20-30% by mass of xanthan gum, and 15-25% by mass of mannan.

Each of the water-soluble sheets (diameter: 300 mm, round shape, thickness: 0.8 mm) in Test Examples 4-1 to 4-4 having the compositions shown in Table 4 was placed on the transparent plate and the gel sheet in the above described Test Example 1-4 was placed thereon. After five minutes, the state of dissolution of the water-soluble sheet was evaluated according to the above described criteria of solubility.

TABLE 3

| | Test Example | | | | | | |
|---|---|---|---|---|---|---|---|
| | 3-1 | 3-2 | 3-3 | 3-4 | 3-5 | 3-6 | 3-7 |
| Polysaccharide thickener composition (*1) | — | 0.5 | 1.0 | 2.5 | 3.0 | 6.0 | 7.0 |
| Glycerin | 5.0 | 5.0 | 5.0 | 5.0 | 5.0 | 5.0 | 5.0 |
| 1,3-butylene glycol | 3.0 | 3.0 | 3.0 | 3.0 | 3.0 | 3.0 | 3.0 |
| Dipropylene glycol | 5.0 | 5.0 | 5.0 | 5.0 | 5.0 | 5.0 | 5.0 |
| PEG-60 hydrogenated castor oil | 0.3 | 0.3 | 0.3 | 0.3 | 0.3 | 0.3 | 0.3 |
| Preservative | Appropriate amount | Appropriate amount | Appropriate amount | Appropriate amount | Appropriate amount | Appropriate amount | Appropriate amount |
| Fragrance | Appropriate amount | Appropriate amount | Appropriate amount | Appropriate amount | Appropriate amount | Appropriate amount | Appropriate amount |
| Water | Balance | Balance | Balance | Balance | Balance | Balance | Balance |
| Water-releasing property (volume of bleeding) | — | Δ | ○ | ○ | ○ | ○ | X |
| Elongation of gel | — | X | ○ | ○ | ○ | ○ | Δ |

(*1): A composition containing 30% by mass of carrageenan, 25% by mass of locust bean gum, 25% by mass of xanthan gum, and 20% by mass of mannan.

As shown in Table 3, in Test Examples 3-3 to 3-6 in which the polysaccharide thickener composition containing 30% by mass of carrageenan, 25% by mass of locust bean gum, 25% by mass of xanthan gum, and 20% by mass of mannan was added at a content within the range of 1 to 6% by mass, the gel sheets demonstrated excellent water-releasing property (volume of bleeding) and elongation (elongation of gel). Among these Test Examples, in Test Examples 3-3 and 3-4 in which the polysaccharide thickener composition was added at 1.0-2.5% by mass, the gel sheets demonstrated especially excellent water-releasing property and elongation.

On the other hand, in Test Example 3-1 in which the above composition was not added, a gel sheet failed to form. In addition, in Test Example 3-2 in which the blending amount In addition, a practical use test (panel: 10 persons) of an external preparation kit composed of the water-soluble sheet in each of the above described Test Examples and the gel sheet in Test Example 1-4 was conducted to evaluate a moist feeling after the external preparation kit was used.

A Moist Feeling

○: Eight or more panels answered that they had a moist feeling on the skin after use Δ: Four or more and less than eight panels answered that they had a moist feeling on the skin after use X: Less than four panels answered that they had a moist feeling on the skin after use

TABLE 4

| | Test Example | | | |
|---|---|---|---|---|
| | 4-1 | 4-2 | 4-3 | 4-4 |
| Hydroxypropyl methylcellulose | 60.0 | 60.0 | 60.0 | 60.0 |
| 1,3-butylene glycol | 15.0 | 10.0 | 3.0 | 3.0 |
| Dipropylene glycol | 5.0 | 8.0 | 8.0 | — |
| Glycerin | — | 3.0 | 7.0 | — |
| PEG-60 hydrogenated castor oil | 1.5 | 1.5 | 1.5 | 1.5 |
| Disodium edetate | 0.1 | 0.1 | 0.1 | 0.1 |
| Preservative | Appropriate amount | Appropriate amount | Appropriate amount | Appropriate amount |
| Water | Balance | Balance | Balance | Balance |
| Moist feeling | ○ | ○ | ○ | Δ |

(Method of Production)

The other components were added to water and then the mixture was mixed by stirring. The resulting aqueous solution was applied to a base and dried to obtain a dry film-like water-soluble sheet.

As shown in Table 4, the dissolution of the water-soluble sheet could provide a moist feeling to the skin when the polyalcohol moisturizing component(s) (1,3-butylene glycol, dipropylene glycol, glycerin) in the water-soluble sheet were added.

What is claimed is:

1. An external preparation kit comprising:
   (I) a gel sheet containing:
      (a) 1-6% by mass of a composition comprising 10-80% by mass of carrageenan, 5-50% by mass of locust bean gum, 5-50% by mass of xanthan gum, and 5-50% by mass of mannan; and
      (b) water; and
   (II) a water-soluble sheet containing one or more component(s) selected from the group consisting of a cellulose derivative, polyvinyl alcohol, collagen, starch, gelatin, agar, and sugar.

2. The external preparation kit according to claim 1 wherein the composition (a) contains carrageenan at 25-35% by mass, locust bean gum at 20-30% by mass, xanthan gum at 20-30% by mass, and mannan at 15-25% by mass.

3. The external preparation kit according to claim 2, wherein a blending amount of the composition (a) is 1-2.5% by mass.

4. The external preparation kit according to claim 2, wherein the (II) water-soluble sheet contains hydroxypropyl methylcellulose.

5. The external preparation kit according to 2, wherein an area of a surface on a side contacting the (II) water-soluble sheet of the gel sheet (I) is larger than an area of a surface on a side contacting the gel sheet of the water-soluble sheet.

6. The external preparation kit according to claim 1 wherein a blending amount of the composition (a) is 1-2.5% by mass.

7. The external preparation kit according to 6 wherein, in the composition, a weight ratio between locust bean gum and xanthan gum is from 2:1 to 1:2.

8. The external preparation kit according to claim 6, wherein the (II) water-soluble sheet contains hydroxypropyl methylcellulose.

9. The external preparation kit according to claim 6, wherein an area of a surface on a side contacting the (II) water-soluble sheet of the gel sheet (I) is larger than an area of a surface on a side contacting the gel sheet of the water-soluble sheet.

10. The external preparation kit according to claim 1 wherein, in the composition, a weight ratio between locust bean gum and xanthan gum is from 2:1 to 1:2.

11. The external preparation kit according to claim 10, wherein the (II) water-soluble sheet contains hydroxypropyl methylcellulose.

12. The external preparation kit according to claim 10, wherein an area of a surface on a side contacting the (II) water-soluble sheet of the gel sheet (I) is larger than an area of a surface on a side contacting the gel sheet of the water-soluble sheet.

13. The external preparation kit according to claim 1, wherein the (II) water-soluble sheet contains hydroxypropyl methylcellulose.

14. The external preparation kit according to claim 13, wherein an area of a surface on a side contacting the (II) water-soluble sheet of the gel sheet (I) is larger than an area of a surface on a side contacting the gel sheet of the water-soluble sheet.

15. The external preparation kit according to claim 1, wherein an area of a surface on a side contacting the (II) water-soluble sheet of the gel sheet (I) is larger than an area of a surface on a side contacting the gel sheet of the water-soluble sheet.

16. A method of using the external preparation kit according to claim 1, comprising:
    laying a gel sheet (I) on a water-soluble sheet (II) so that the gel sheet (I) covers a whole surface on one side of the water-soluble sheet (II) completely.

17. A method of using the external preparation kit according to claim 2, comprising:
    laying a gel sheet (I) on a water-soluble sheet (II) so that the gel sheet (I) covers a whole surface on one side of the water-soluble sheet (II) completely.

18. A method of using the external preparation kit according to claim 6, comprising:
    laying a gel sheet (I) on a water-soluble sheet (II) so that the gel sheet (I) covers a whole surface on one side of the water-soluble sheet (II) completely.

19. A method of using the external preparation kit according to claim 10, comprising:
    laying a gel sheet (I) on a water-soluble sheet (II) so that the gel sheet (I) covers a whole surface on one side of the water-soluble sheet (II) completely.

20. A method of using the external preparation kit according to claim 13, comprising:
    laying a gel sheet (I) on a water-soluble sheet (II) so that the gel sheet (I) covers a whole surface on one side of the water-soluble sheet (II) completely.

* * * * *